(12) United States Patent
Kahana et al.

(10) Patent No.: US 8,673,369 B2
(45) Date of Patent: Mar. 18, 2014

(54) FRUIT AND VEGETABLE-DERIVED COMPOSITIONS

(75) Inventors: Yehuda Kahana, Herzelia (IL); Rami Maimon, Holon (IL); Chaim Perry, Tel Aviv (IL)

(73) Assignee: Secret of Youth Ltd., Or Yehuda (IL)

( * ) Notice: Subject to any disclaimer, the term of this patent is extended or adjusted under 35 U.S.C. 154(b) by 0 days.

(21) Appl. No.: 13/145,896

(22) PCT Filed: Jan. 24, 2010
(Under 37 CFR 1.47)

(86) PCT No.: PCT/IL2010/000058
§ 371 (c)(1),
(2), (4) Date: Mar. 9, 2012

(87) PCT Pub. No.: WO2010/084496
PCT Pub. Date: Jul. 29, 2010

(65) Prior Publication Data
US 2013/0101691 A1    Apr. 25, 2013

(30) Foreign Application Priority Data

Jan. 25, 2009   (IL) .......................................... 196695

(51) Int. Cl.
*A01N 65/00*    (2009.01)

(52) U.S. Cl.
USPC ........................................................ 424/725

(58) Field of Classification Search
None
See application file for complete search history.

(56) References Cited

U.S. PATENT DOCUMENTS

| | | |
|---|---|---|
| 4,255,418 A | 3/1981 | Bailey |
| 5,674,497 A | 10/1997 | Kuwana et al. |
| 5,674,510 A | 10/1997 | DiTucci |
| 6,063,381 A | 5/2000 | Staggs |
| 6,780,444 B1 | 8/2004 | Reza |
| 2004/0061142 A1 | 4/2004 | Raman et al. |
| 2005/0048145 A1 | 3/2005 | Azik |
| 2005/0090557 A1 | 4/2005 | Muhammad et al. |
| 2008/0317936 A1 | 12/2008 | Magliba |

FOREIGN PATENT DOCUMENTS

| | | |
|---|---|---|
| DE | 43 12 109 A1 | 10/1994 |
| WO | 00/02544 A2 | 1/2000 |
| WO | 02/07746 A1 | 1/2002 |
| WO | 2004/008887 A1 | 1/2004 |
| WO | 2005/062713 A2 | 7/2005 |
| WO | 2006/060470 A1 | 6/2006 |

OTHER PUBLICATIONS

Jun et al., "Capsaicin induced apoptosis of B16-F10 melanoma cells through down-regulation of Bcl-2," *Food and Chemical Toxicology* 45:708-715, 2007.

Kapadia et al., "Chemoprevention of lund and skin cancer by *Beta vulgaris* (beet) root extract.," *Cancer Letters* 100(1-2):211-214, Feb. 27, 1996, 1 page. (Abstract only).

English Translation of First Office Action for corresponding Chinese Patent Application No. 201080005422.8, mailed Sep. 28, 2012, 12 pages.

First Office Action for corresponding Chinese Patent Application No. 201080005422.8, mailed Sep. 28, 2012, 12 pages.

Chen, "Food prohibition for the prevention of acne," *Woman Health Care*, Democracy and Construction Press, Beijing, 2nd edition, p. 306, with English translation, 2 pages, Jun. 30, 2005.

English Translation of Second Office Action for corresponding Chinese Patent Application No. 201080005422.8, mailed Aug. 1, 2013, 11 pages.

*Primary Examiner* — Michael Meller
(74) *Attorney, Agent, or Firm* — Seed IP Law Group PLLC

(57) ABSTRACT

This invention provides fruit and vegetable-derived compositions comprising a fruit or vegetable derivative of inter alia, at least one *Beta*, *Capsicum* and *Malus* species, wherein the composition is at a pH in the range of about 3 to about 6.5. The invention further provides for process for the production of the same and uses thereof.

18 Claims, No Drawings

FRUIT AND VEGETABLE-DERIVED COMPOSITIONS

FIELD OF THE INVENTION

The present invention is directed to compositions derived from fruits and vegetables suitable for topical application. In particular the present invention relates to a fruit and vegetable derived composition suitable for topical application to the skin to treat and prevent dermatological disorders and for cosmetic applications. The present invention also relates to a process for preparing such fruit and vegetable derived composition.

BACKGROUND OF THE INVENTION

Skin disease afflicts millions of individuals annually. Although various compounds and active ingredients beneficial to the skin have been identified, and multiple formulations have been deduced, an ideal skin product, which effectively treats these conditions or disorders has not been developed. Skin care products formulated primarily from substances that have been formed or extracted from natural botanical products have great appeal. Such formulations are thought to provoke fewer adverse skin reactions, and potentially to be effective in combating skin disease.

Nevertheless, it is generally acknowledged that there is no one single effective substance or remedy for skin diseases or disorders nor is there an ideal skin cosmetic.

Topical application and/or oral ingestion of Vitamins A (CAS CAS 68-26-8), C (ascorbic acid, CAS 50-81-7) and E (d-α-tocopherol, CAS 59-02-9), has been shown to provide protection against various chemicals, including free radicals. Citric acid, malic acid and tartaric acid are the prominent acids in fruits and to some degree vegetables. They are usually referred to as alpha and/or beta-hydroxy acids. Other similar ingredients are alpha hydroxy acids like glycolic acid or lactic acid.

The exfoliating effects of such acids depend very much on the concentration of the acids and the pH. The art to date, however, has taught that acidic topical compositions are associated with an increase in deleterious skin side effects resulting in skin becoming red, swollen, and sensitive and forming blisters. Rashes and itching may occur. Exposure to the sunlight will exacerbate such reactions.

Since 1989 the US Food and Drug Administration (FDA) has received more than 100 reports of adverse reactions in people using alpha hydroxy acid products. Based on past experience with complaints the FDA extrapolates from these 100 complaints that there have been approximately 10,000 adverse reactions. Products containing alpha hydroxy acids will be either regulated as cosmetics, or drugs or both depending on their intended use. In particular, pharmaceutical effects after penetration of the skin barrier, like increasing cell-turnover rate, rejuvenescence, skin softening and decreasing thickness of the outer skin are of concern to the FDA. These effects depend on the acidity, the concentration of the acids, and the cosmetic carrier.

Further, many fruit-based products topically applied to the skin have a pH in the acidic range and can cause irritation to the skin.

There therefore exists a need for a topically applied composition and process for preparing the same, which effectively treats dermatological disorders yet does not suffer from these limitations.

SUMMARY OF THE INVENTION

In one embodiment, this invention provides a fruit and vegetable-derived composition comprising a derivative of at least one *Beta, Capsicum* and *Malus* species at a pH in the range of about 3 to about 6.5.

In some embodiments, according to this aspect, the fruit and vegetable-derived composition further comprises a derivative of at least one *Solanum, Cucumis*, a *Citrus limon*, a *Citrus paradisi* and a Prunus. In some embodiments, according to this aspect, the fruit and vegetable-derived composition further comprises a derivative of a Diospyros. In some embodiments, according to this aspect, the fruit and vegetable-derived composition further comprises a derivative of a *Citrus maxima*. In some embodiments, according to this aspect, the fruit and vegetable-derived composition further comprises a derivative of a *Carica papaya*.

In some embodiments, the invention provides a fruit and vegetable-derived composition comprising a fruit or vegetable derivative of at least one *Beta* species, present at a concentration of 0.1-5% w/w, at least one *Capsicum* species, present at a concentration of 0.1-5% w/w and at least one *Malus* species present at a concentration of 1.5-10% w/w in said composition. In some embodiments, according to this aspect, the fruit and vegetable-derived composition further comprises an additional derivative of at least one Solanum species, at least one Cucumis, at least one *Citrus limon* or at least one *Citrus paradisi* or a combination thereof and in some embodiments, the at least one Solanum species is present at a concentration of 1.0-10% w/w, at least one Cucumis species is present at a concentration of 0.1-10% w/w, at least one *Citrus limon* species is present at a concentration of 2.0-10% w/w, at least one *Citrus paradisi* is present at a concentration of 2.0-10% w/w in said composition. In some embodiments, according to this aspect, the fruit and vegetable-derived composition further comprises an additional derivative of a Diospyros species present at a concentration of 1.0-10% w/w in said composition. In some embodiments, according to this aspect, the fruit and vegetable-derived composition further comprises an additional derivative of a *Carica papaya* species present at a concentration of 0.1-5% w/w in said composition.

In some embodiments, according to this aspect, the whole fruit or a derivative comprises a pulp and a seed of said fruit and optionally a zest, a peel or a combination thereof of said fruit. In some embodiments, according to this aspect, the whole vegetable derivative comprises a pulp of said vegetable and a peel of said vegetable.

In some embodiments, this invention provides a process for preparing fruit and vegetable-derived composition comprising the steps of:

a) mixing a whole fruit and vegetable derivative comprising a whole fruit or vegetable derivative of at least one *Beta, Capsicum* and *Malus* species with water at a temperature in the range of about 85° C. to 100° C.; and b) adjusting a pH of said fruit and vegetable-derived composition in (a) to a range of about 3 to about 6.5.

In some embodiments, according to this aspect, the process further comprises the step of filtering the heated fruit and vegetable derivative in (a) at a temperature in the range of about 70° C. to 90° C. to form a filtered fruit and vegetable derivative. In some embodiments, according to this aspect, the process further comprises the step of cooling said filtered derivative to a temperature in the range of about 40° C. to 50° C. and adding stabilizers, preservatives and optionally other additives to form a fruit and vegetable-derived composition. In some embodiments, according to this aspect, the process further comprises the step of freezing and thawing the composition in (a) prior to said filtering.

In some embodiments, the invention provides a composition prepared according to a process of the invention.

In some embodiments, the invention provides for the use of an effective amount of a fruit and vegetable-derived composition of this invention for the preparation of a topical medicament for the treatment or prophylaxis of a dermatologic disease or disorder in a mammal. In some embodiments, according to this aspect, the dermatologic disease or disorder is psoriasis, acne, seborrhea, eczema, skin erosion, skin inflammation, hair loss, diabetic ulcers or lesions, wrinkles or skin fissures. In some embodiments, according to this aspect, the dermatologic disease or disorder is skin neoplasia.

DETAILED DESCRIPTION OF THE PRESENT INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

The present invention relates, in some embodiments, to a fruit and vegetable-derived composition comprising a derivative of at least one *Beta, Capsicum* and *Malus* species. In some embodiments, such fruit and vegetable-derived composition has a final pH in the range of about 3 to about 6.5. In some embodiments, such fruit and vegetable-derived composition has a final pH in the range of about 3 to about 4.5, or in some embodiments, such composition will have a final pH in the range of about 4 to about 4.75, or in some embodiments, such composition will have a final pH in the range of about 4.5 to about 5.25, or in some embodiments, such composition will have a final pH in the range of about 5 to about 5.50, or in some embodiments, such composition will have a final pH in the range of about 5.25 to about 6.50.

In some embodiments, said composition comprises said at least one *Beta* species, present at a concentration of 0.1-5% w/w, at least one *Capsicum* species, present at a concentration of 0.1-5% w/w and at least one *Malus* species present at a concentration of 1.5-10% w/w in said composition.

In some embodiments, said composition comprises said at least one *Beta* species, present at a concentration of 0.2-2% w/w, or in some embodiments, said composition comprises said at least one *Beta* species, present at a concentration of 0.5-4% w/w, or in some embodiments, said composition comprises said at least one *Beta* species, present at a concentration of 2-6% w/w, or in some embodiments, said composition comprises said at least one *Beta* species, present at a concentration of 2.5-8% w/w In some embodiments, said composition comprises t least one *Capsicum* species, present at a concentration of 0.1-5% w/w, or in some embodiments, said composition comprises t least one *Capsicum* species, present at a concentration of 0.2-2% w/w, or in some embodiments, said composition comprises t least one *Capsicum* species, present at a concentration of 0.5-4% w/w, or in some embodiments, said composition comprises t least one *Capsicum* species, present at a concentration of 2-6% w/w, or in some embodiments, said composition comprises t least one *Capsicum* species, present at a concentration of 3-10% w/w.

In some embodiments, said composition comprises at least one *Malus* species present at a concentration of 1.5-10% w/w in said composition, or in another embodiment, said composition comprises at least one *Malus* species present at a concentration of 3-5.75% w/w, or in another embodiment, said composition comprises at least one *Malus* species present at a concentration of 2.75-4.75% w/w, or in another embodiment, said composition comprises at least one *Malus* species present at a concentration of 5-8.5% w/w, or in another embodiment, said composition comprises at least one *Malus* species present at a concentration of 1.5-3% w/w, or in another embodiment, said composition comprises at least one *Malus* species present at a concentration of 7-10% w/w, or in another embodiment, said composition comprises at least one *Malus* species present at a concentration of 2.5-6% w/w.

The term "derivative" refers in some embodiments, to incorporation of at least a part of a pulp within the compositions of the invention, and in some embodiments, refers to incorporation of the whole fruit or vegetable, respectively. In some embodiments, the term "derivative" refers to incorporation of a seed of the indicated fruit in the composition, or in some embodiments, the term "derivative" refers to incorporation of a zest of the indicated fruit within the composition, or in some embodiments, the term "derivative" refers to incorporation of some parts of the peel and/or some part of the seed of the indicated fruit within the composition, or in some embodiments, the term "derivative" refers to incorporation of a combination of any of the fruit components as described herein or in some embodiments, the entire contents of the indicated fruit. It is to be understood that the term "derivative" refers to at least the incorporation of a fruit pulp, or the incorporation of a fruit zest or peel and a fruit seed in the compositions of this invention, and may include incorporation of any other part of the fruit, or the whole fruit including all its components, as will be appreciated by the skilled artisan, including the juice of the fruit. In some embodiments, the term "derivative" refers to any extract of the fruit and/or vegetable.

The term "derivative" refers, in some embodiments, to incorporation of at least a part of a vegetable pulp within the compositions of the invention and in some embodiments, refers to incorporation of the whole vegetable contents in the compositions of the invention. In some embodiments, the term "derivative" refers to incorporation of a peel of said vegetable, or in some embodiments, to a root, leaf, branch or a seed of said vegetable, or in some embodiments, incorporation of a combination thereof. It is to be understood that the term "derivative" refers to at least the incorporation of a vegetable pulp, or the incorporation of a vegetable peel and a vegetable branch, root, leaf or seed in the compositions of this invention, or the incorporation of any part of the vegetable or all parts of the vegetable, and may include incorporation of any other part of the vegetable, as will be appreciated by the skilled artisan, including the juice of the vegetable.

The pulp may be derived from an inner fleshy part of the fruit or vegetable, or alternatively, from a mixture of the skin and an outer fleshy part of the fruit or vegetable. In some cases, and depending on the type of fruit or vegetable, the whole fruit or vegetable may be pulped. In other cases, and again depending on the type of fruit or vegetable, just the skin of the fruit or vegetable may be pulped.

In some embodiments, vitamin concentration may be assessed and batches of said fruit and vegetable-derived composition may be normalized based on a concentration of such vitamins. For example, and in some embodiments, vitamin C, vitamin A, B complex vitamins and/or vitamin E concentration can be measured and compositions may be adjusted, including ratios of inclusion of particular derivatives may be adjusted to reflect the concentration of the vitamins assessed.

In some embodiments, the compositions of this invention may comprise additional fruit or vegetable derivatives as described, for example, and in some embodiments, the compositions may further comprise derivatives as described herein, further comprising derivatives of a peach, pawpaw, mango, lime, mandarin, grape, orange, passion fruit, plum, pineapple, pear, avocado, potato, pumpkin, carrot, lettuce, cabbage, apricot, melon including watermelon and rock melon, grapefruit, berry including strawberry, blueberry, mulberry or raspberry, and banana In some embodiments, the fruit or vegetable from which the derivative is prepared is used when fresh and raw, or in some embodiments is frozen, including flash frozen, or is steamed or blanched and preserved. In some embodiments, fermentation products of the fruit and/or vegetable are used. In some embodiments, fruits and/or vegetables which are raw, steamed, cooked, or processed in any way may be incorporated in the compositions of this invention.

In some embodiments, the skin of the fruit or vegetable is removed prior to pulping and in some embodiments, pulping of the flesh of the fruit or vegetable, is conducted separately from that of other parts of the fruit and vegetable. In some embodiments, pulping of each species of fruit and vegetable is conducted separately, and in some embodiments, pulping of all flesh of various species of fruits and vegetables utilized is conducted together. For example, apple flesh can be pulped separately and utilized in the process of the present invention, and apple skin can also be pulped separately.

In some embodiments, the fruit and vegetable-derived compositions of this invention comprise a whole derivative of at least one *Beta, Capsicum* and *Malus* species and optionally a citrus fruit derivative.

In some embodiments, the fruit and vegetable-derived derivatives are processed separately and then combined, or in some embodiments, processed in combination, following which the derivatives are combined with boiling water. In some embodiments, the derivatives are combined with boiling water separately, and the multiple processed derivatives are combined. In some embodiments, the derivatives are then filtered. In some embodiments, filtration is conducted following minimal cooling of the derivative/water mixtures. In some embodiments, cooling is by up to 20° C., or in some embodiments, cooling is to a temperature at a range of about 70 to about 85° C. In some embodiments, following filtration and minimal cooling, further cooling is conducted. In some embodiments, cooling is to a temperature at a range of about 40 to about 55° C., or in some embodiments, cooling may be to room temperature. In some embodiments, following cooling additional additives may be incorporated, as appreciated by the skilled artisan, and exemplified and described in part hereinbelow.

In some embodiments, filtration of each fruit and vegetable derivative is accomplished separately, after which the filtered derivatives are combined. In some embodiments, the derivatives are combined prior to filtration.

In some embodiments, the term "pulp" or grammatical forms thereof, refer to a processing of the indicated fruit or vegetable part, such as the flesh of such fruit or vegetable, to include maceration to form of a viscous liquid or puree or other processed forms understood to be encompassed by the skilled artisan as comprising the "pulp" of the indicated fruit and/or vegetable. In some embodiments, a food processor or blender or other mechanical apparatus may be used to pulp the fruit and/or vegetable flesh. As stated above in some instances, a mixture of fruit flesh and skin and/or vegetable flesh and skin and optionally seed or stone or pip is processed to a pulp in the form of a viscous liquid. In some embodiments, such seed, stone or pip may be ground or pulverized prior to combination with other fractions or sections of the fruit or vegetable.

In some embodiments, the derivatives will comprise at least one *Beta, Capsicum* and *Malus* species.

In some embodiments, the *Beta* product will comprise a derivative of a *Beta* species, including *Beta vulgaris*, or the garden beet. In some embodiments, the *Beta* product will comprise chard and spinach beet, as well as sugar beet, and mangelwurzel.

In some embodiments, *Capsicum* species will include *Capsicum annuum*, including bell peppers, paprika, cayenne, jalapeños, and the chiltepin, *Capsicum frutescens*, which includes the tabasco peppers, *Capsicum chinense*, which includes the naga, habanero, Datil and Scotch bonnet peppers, *Capsicum pubescens*, which includes the South American rocoto peppers and *Capsicum baccatum* and various cultivars.

In some embodiments, *Malus* species will include *Malus domestica, M. sieversii, Malus baccata* and *Malus sylvestris* and various cultivars thereof.

In some embodiments, the composition will further comprise a derivative of at least one Solanum species, which may comprise *Solanum lycopersicum*, and various cultivars thereof.

In some embodiments, the composition will further comprise a derivative of at least one Cucumis species, which may comprise *Cucumis sativus*, and various cultivars thereof.

In some embodiments, the composition will further comprise a derivative of at least one citrus fruit, including a *Citrus limon*, a *Citrus paradisi*, a *Citrus aurantifolia*, a *Citrus maxima*, a *Citrus medica* and a *Citrus reticulata*.

In some embodiments, the composition will further comprise a derivative of at least one Prunus species, including *Prunus persica* and cultivars thereof.

In some embodiments, the composition will further comprise a derivative of at least one Diospyros species, including *Diospyros kaki* or *Diospyros lotus* and cultivars thereof.

In some embodiments, the composition will further comprise a derivative of at least one *Carica papaya*.

In some embodiments, the compositions of this invention are particularly useful for applications in rejuvenating and renewing skin.

The composition of the present invention may be prepared by first pulping the selected fruit and/or vegetable to a viscous liquid pulp, then heating the fruit and/or vegetable pulp to a temperature above about 60-90° C., which in some embodiments is accomplished by combining the processed fruit and vegetable derivative and combining the derivative with boiling water, and optionally additionally heating the combined water and derivative mixture.

In some embodiments, heating may be accomplished by any means such as a microwave, or an electric or gas stove, or by use of a double boiler in a stove.

In some embodiments, following heating of the derivatives the derivatives may be beaten, or in some embodiments, the derivatives may be combined and beaten. In some embodiments, the beating facilitates the aeration of the mixture and improvement of the consistency of the final product. In some embodiments, such beating or other mixing step is performed at any stage following preparation of the derivatives, and formation of the final product.

In some embodiments, following initial processing of the fruit and/or vegetable components to form a derivative, such derivative may be frozen, or in some embodiments, following further processing of the derivative to include mixing with water as described herein, and/or adding the indicated additives to said mixture, the product may be frozen and stored for an indefinite period of time. In some embodiments, following initial processing of the fruit and/or vegetable components to form a derivative, such derivative may be stored at 2-10° C. or at room temperature, or in some embodiments, following further processing of the derivative to include mixing with water as described herein, and/or adding the indicated additives to said mixture, the product may be stored at 2-10° C., or at room temperature for a few days, or in some embodiments, for an extended period of time, In some embodiments, the composition has a gel-like consistency, or in some embodiments, the composition when fully processed has a foam consistency.

In some embodiments, following preparation of a fruit or vegetable derivative, each derivative or combined derivatives are filtered via any means known in the art. In some embodiments, filtration is through a sieve, or in some embodiments calico or other similar fabric over a period of hours, for example, in some embodiments, about 12 to 24 hours, or in some embodiments filtration may be conducted over a period of days. Other filtration methods/devices can also typically be utilized.

In some embodiments, the compositions of this invention will have a pH, which is acidic, which in some embodiments, is in the range of about 3 to about 6.5. In some embodiments, the pH of the composition is in the range of about 4 to 6. In some embodiments, the pH of the composition is in the range of about 4.5 to 5.75. In some embodiments, the pH of the composition is in the range of about 4.2 to 5.5. The pH may be measured by a pH meter throughout the manufacturing process.

In some embodiments, the pH of the composition may be adjusted by the addition of a mild acid, as will be appreciated by the skilled artisan. In some embodiments, the amount of mild acid which is to be added can be calculated according to the acidity of each batch of fruit and/or vegetable pulp and the end pH in the range that is desired.

In some embodiments, preservative can be added to the composition, including conventional natural preservatives, or in some embodiments, inclusion of certain fractions of the fruit and/or vegetable obviates the necessity for adding a preservative, for example, the incorporation of grapefruit seed in the derivative may accomplish the same.

In some embodiments, the compositions of the present invention are formulated as a soap, gel, cream, lotion, ointment or the like. In some embodiments, such compositions may comprise any suitable pharmaceutically acceptable carrier or excipient, as will be appreciated by the skilled artisan. In some embodiments, such carriers may include deionised water, vegetable or mineral oils, white petrolatum, branched chain fats or oils, animal fats, vegetable fats and/or butters, and high molecular weight alcohol. Emulsifiers, stabilizers and antioxidants may also be included as well as coloring agents and essential oils to impart fragrance.

In some embodiments, the compositions of the present invention can be formulated as a lotion or tonic. The compositions can also be formulated as creams or ointments. In such formulations the active composition may be added in an amount of 10% to 60% w/w of base moisturizer cream and mixed in with the base cream. For example, sorbolene cream or other moisturizers can have compositions of the present invention added to them in an amount of 10% to 60% w/w. Alternatively, macadamia oil, jojoba oil, almond oil or other nut and seed oils may be have the active composition of the present invention added to them in an amount of 10% to 60% w/w Other topical products in which the compositions of the present invention can be formulated include skin care products such as creams, gels, pastes, emulsions, salves, exfoliants, cleansers, toners, sprays, masques and peels, sunscreens, lip balms, lipsticks, depilatories, facial and body soaps and the like. In some embodiments, bandages or patches impregnated with the compositions of this invention are envisioned as formulations of this invention, for example for use in wound healing compositions for certain skin lesions or ulcerations.

Suitable topical vehicles for use with the formulations of the present invention are well known in the cosmetic and pharmaceutical areas and include water, lipid bases materials including oils and fats, soaps, surfactants, emollients, skin conditioning agents and emulsifying agents. Examples of these vehicles are described Martindale—The Extra Pharmacopoeia (Pharmaceutical Press). Clearly, the choice of a suitable vehicle depends on the mode of delivery of the formulation. The active composition is generally incorporated in the dermatologically/cosmetically acceptable vehicle/carrier in a conventional manner well known in the cosmetic and pharmaceutical arts.

As used herein, "pharmaceutical composition" means a "therapeutically effective amount" of the active ingredient, i.e. the fruit and vegetable derivatives of this invention, together with a pharmaceutically acceptable carrier or diluent. A "therapeutically effective amount" as used herein refers to that amount which provides a therapeutic effect for a given condition and administration regimen.

In some embodiments, this invention provides compositions which may comprise at least one of the indicated fruit- and vegetable-derived products of the present invention, in any form or embodiment as described herein. In some embodiments, the term "a" is to be understood to encompass a single or multiple of the indicated material. In some embodiments, the term "a" or "an" refers to at least one.

In some embodiments, any of the compositions of this invention will consist of a fruit and vegetable product of this invention, in any form or embodiment as described herein. In some embodiments, of the compositions of this invention will consist essentially of a fruit and vegetable product of this invention, in any form or embodiment as described herein.

In some embodiments, the term "comprise" and grammatical forms thereof refers to the inclusion of the indicated derivative, as well as inclusion of other active agents, and pharmaceutically acceptable carriers, excipients, emollients, stabilizers, etc., as are known in the pharmaceutical industry. In some embodiments, any of the compositions of this invention will comprise at least a derivative of a *Beta, Capsicum* and *Malus* species in any form or embodiment as described herein. In some embodiments, any of the compositions of this invention will consist of a derivative of a *Beta, Capsicum* and *Malus* species, in any form or embodiment as described herein. In some embodiments, of the compositions of this invention will consist essentially of a derivative of a *Beta, Capsicum* and *Malus* species, in any form or embodiment as described herein. In some embodiments, the term "comprise" refers to the inclusion of the indicated active agent, such as the derivative of a *Beta, Capsicum* and *Malus* species, as well as inclusion of other active agents, and pharmaceutically acceptable carriers, excipients, emollients, stabilizers, etc., as are known in the pharmaceutical industry. In some embodiments, the term "consisting essentially of" refers to a composition, whose only active ingredient is the indicated active ingredient, however, other compounds may be included which are for stabilizing, preserving, etc. the formulation, but are not involved directly in the therapeutic effect of the indicated active ingredient. In some embodiments, the term "consisting essentially of" refers to a composition, whose only active ingredient with a comparable mode of action, or comparable molecular target is the indicated active ingredient, however, other active ingredients may be incorporated, with such secondary active ingredients acting on different targets, or in a palliative capacity. In some embodiments, the term "consisting essentially of" may refer to components which facilitate the release of the active ingredient. In some embodiments, the term "consisting" refers to a composition, which contains a compound as herein described as the only active ingredient and a pharmaceutically acceptable carrier or excipient.

Topical application of an efficacious amount of the fruit- and vegetable-derived product of the present invention to an area of skin in need of treatment affords fast and effective relief from the symptoms of various dermatological disorders including psoriasis, eczema, dry skin, wrinkles, and acne. The area of treated skin takes on an improved skin tone and appears smoother and more taut. Dry and flaking skin is exfoliated from the surface of the skin, and inflamed and reddened skin is soothed.

While the art has taught that acidic formulations typically cause inflammation of the skin and damage thereto, surprisingly, Applicants have found that use of specific combinations of fruit and vegetable derivatives in the compositions of this invention are specifically useful in treating skin inflammatory conditions in general. Such treatment of skin inflammation and other skin diseases is unexpected therefore and represents a marked improvement to prior formulations. In some embodiments, a minimal skin reaction occurs at the time of administration, however, such reaction disappears within hours of administration and does not negate the positive effect of the product. In some embodiments, the minimal skin reaction includes a minor rash, redness or swelling. In some embodiments, the minimal skin reaction disappears within 2 hours of administration, or in some embodiments, within 4 hours of administration, or in some embodiments, does not persist beyond 12 hours post-administration.

Moreover, the invention describes that certain combinations of fruits and vegetable derivatives in an acidic environment specifically are useful in treating skin conditions. The invention also surprisingly enables treatment of skin diseases as described herein as a function of the ratio of inclusion of the particular fruit and vegetable derivatives as herein described.

In some embodiments, the compositions of the present invention are topically applied to an animal, which in some embodiments is a human, which are appropriate for males and females of the species.

In some embodiments, the compositions are applied for the treatment or prophylaxis of all epidermal disorders including psoriasis, eczema, insect bites, general epidermal irritation and redness including rosacea and itchiness, alopecia, circulatory disorders affecting the epidermis, sunburn, windburn and first, second and third degree burns, healing of sores, wounds and skin infections, bed sores, pressure sores, skin cancers including sunspots, skin melanomas, and also alleviates some gum diseases and mouth ulcers and other gum and mouth dermatological disorders. In some embodiments, the compositions of the invention are applied for the treatment or prophylaxis of acne, seborrhea, skin erosion, skin inflammation, hair loss, diabetic ulcer or other skin lesion, wrinkles or skin fissures. It can also be applied to prevent sunburn. In some embodiments, the compositions of this invention are useful for the treatment or prophylaxis of aging of the skin such as dermal atrophy and thinning, elastolysis sebaceous gland hyperplasia or hypoplasia, senile lentigo, pigmentation abnormalities, graying of hair and hair loss or thinning (baldness, alopecia), chronic skin ulcers, healing of wounds, burns, abrasions or other acute or chronic conditions of epidermis.

In some embodiments, the compositions of the present invention can be topically applied, particularly to the face and hands and neck to achieve an enhanced cosmetic benefit. In some embodiments, the composition of the present invention can be applied topically to the epidermis as an exfoliant, as an effective astringent or antibacterial, as well as an excellent skin cleanser and freshener. A general improvement in clarity, skin texture and appearance is observed after application of a composition of the present invention.

In some embodiments, one or more pure compositions of the present invention is topically applied to the area of skin in need of treatment, allowed to penetrate the skin for a period of up to typically 20 to 90 minutes, more typically 45 minutes. In some embodiments, the composition may be removed from the skin by rinsing with water, or other absorption means, for example by a wipe or towel.

In some embodiments, other compositions may be applied to the skin following application of the compositions of this invention, and in some embodiments, additional active ingredients may be incorporated within the compositions of this invention. Such additional active ingredients may comprise antibacterial compounds, antifungal compounds, antiseptics, analgesics, purified vitamins, extracellular matrix proteins and other known skin healing compounds.

In some embodiments, the compositions of the present invention can be in the form of a 'wash-off' product such as a masque or lotion or gel, or can be formulated as a product to be left on such as a cream or ointment.

The present inventive method of processing the fruit and/or vegetable derivatives provides a new and useful composition.

The pulped fruit and/or vegetable material will typically contain carbohydrates (sugars) particularly glucose, fructose, maltose and sucrose.

In one embodiment, the terms "treating" or "treatment" includes preventive as well as disorder remissive treatment. In some embodiments, the uses and methods of this invention provide for the reducing of pathogenesis of the diseases or disorders as described herein and/or reducing the severity of the diseases and/or disorders as described herein, and/or reducing or inhibiting or suppressing the symptoms associated with the diseases or disorders as described herein. The terms "reducing", "suppressing" and "inhibiting" have their commonly understood meaning of lessening or decreasing, in another embodiment, or delaying, in another embodiment, or reducing, in another embodiment the incidence, severity or pathogenesis of a disease, disorder or condition. In embodiment, the term treatment refers to delayed progression of, prolonged remission of, reduced incidence of, or amelioration of symptoms associated with the disease, disorder or condition. In one embodiment, the terms "treating" "reducing", "suppressing" or "inhibiting" refer to a reduction in morbidity, mortality, or a combination thereof, in association with the indicated disease, disorder or condition. In one embodiment, the term "progression" refers to an increasing in scope or severity, advancing, growing or becoming worse. The term "recurrence" means, in another embodiment, the return of a disease after a remission. In one embodiment, the methods of treatment of the invention reduce the severity of the disease, or in another embodiment, symptoms associated with the disease, or in another embodiment, reduces the number of biomarkers expressed during disease.

In one embodiment, the term "treating" and its included aspects, refers to the administration to a subject with the indicated disease, disorder or condition, or in some embodiments, to a subject predisposed to the indicated disease, disorder or condition. The term "predisposed to" is to be considered to refer, inter alia, to a genetic profile or familial relationship which is associated with a trend or statistical increase in incidence, severity, etc. of the indicated disease. In some embodiments, the term "predisposed to" is to be considered to refer, inter alia, to a lifestyle which is associated with increased risk of the indicated disease. In some embodiments, the term "predisposed to" is to be considered to refer, inter alia, to the presence of biomarkers which are associated with the indicated disease, for example, in cancer, the term "predisposed to" the cancer may comprise the presence of precancerous precursors for the indicated cancer.

In some embodiments, the term "reducing the pathogenesis" is to be understood to encompass reducing tissue damage, or organ damage associated with a particular disease, disorder or condition. In another embodiment, the term "reducing the pathogenesis" is to be understood to encompass reducing the incidence or severity of an associated disease, disorder or condition, with that in question. In another embodiment, the term "reducing the pathogenesis" is to be understood to encompass reducing the number of associated diseases, disorders or conditions with the indicated, or symptoms associated thereto.

The term "administering", in another embodiment, refers to bringing a subject in contact with a compound of the present invention. Administration can be accomplished in vitro, i.e. in a test tube, or in vivo, i.e. in cells or tissues of living organisms, for example humans. In one embodiment, the present invention encompasses administering the compounds of the present invention to a subject.

In one embodiment, the methods of this invention make use of the described compound of this invention contacting diseased skin or in some embodiments, afflicted skin or in some embodiments, skin at risk for such affliction in an amount effective to treat and/or prevent the indicated disease and/or disorder and thereby mediate the described effects.

In another embodiment, the compositions of this invention comprise one or more, pharmaceutically acceptable carrier materials.

In one embodiment, the carriers for use within such compositions are biocompatible, and in another embodiment, biodegradable. In other embodiments, the formulation may provide a relatively constant level of release of one active component. In other embodiments, however, a more rapid rate of release immediately upon administration may be desired. In other embodiments, release of active compounds may be event-triggered. The events triggering the release of the active compounds may be the same in one embodiment, or different in another embodiment. Events triggering the release of the active components may be exposure to moisture in one embodiment, lower pH in another embodiment, or temperature threshold in another embodiment. The formulation of such compositions is well within the level of ordinary skill in the art using known techniques. Illustrative carriers useful in this regard include microparticles of poly (lactide-co-glycolide), polyacrylate, latex, starch, cellulose, dextran and the like. Other illustrative postponed-release carriers include supramolecular biovectors, which comprise a non-liquid hydrophilic core (e.g., a cross-linked polysaccharide or oligosaccharide) and, optionally, an external layer comprising an amphiphilic compound, such as phospholipids. The amount of active compound contained in one embodiment, within a sustained release formulation depends upon the site of administration, the rate and expected duration of release and the nature of the condition to be treated suppressed or inhibited.

In another embodiment, it will be preferable to include isotonic agents, for example, sugars or sodium chloride. In other embodiments, prolonged absorption of the injectable compositions will be desirable. Prolonged absorption of the injectable compositions can be brought about by the use of agents delaying absorption, for example, aluminum monostearate and gelatin, in the compositions.

In some embodiments, the individual or combined derivatives of this invention may be administered at different dosages, as a function of time, or disease/symptom/condition severity, or age, or other factors, as will be appreciated by one skilled in the art.

While the fruit and vegetable derivatives of the invention can be administered as the sole active pharmaceutical agent, they can also be used in combination with one or more other compound, and/or in combination with other agents used in the treatment and/or prevention of the diseases, disorders and/or conditions, as will be understood by one skilled in the art. In another embodiment, the compounds of the present invention can be administered sequentially with one or more such agents to provide sustained therapeutic and prophylactic effects. In another embodiment, the compounds may be administered via different routes, at different times, or a combination thereof.

In addition, the compounds of the present invention can be used, either singly or in combination, in combination with other modalities for preventing or treating conditions, diseases or disorders. In some embodiments, such other treatment modalities may include without limitation, surgery, radiation, hormone supplementation, diet regulation, wound debridement, etc., as will be appropriate for the condition being treated. These can be performed sequentially (e.g., treatment with a compound of the invention following surgery or radiation) or in combination (e.g., in addition to a diet regimen).

The additional active agents may generally be employed in therapeutic amounts as indicated in the PHYSICIANS' DESK REFERENCE (PDR) 53rd Edition (1999), or such therapeutically useful amounts as would be known to one of ordinary skill in the art. The compounds of the invention and the other therapeutically active agents can be administered at the recommended maximum clinical dosage or at lower doses. Dosage levels of the active compounds in the compositions of the invention may be varied to obtain a desired therapeutic response depending on the route of administration, severity of the disease and the response of the patient. The combination can be administered as separate compositions or as a single dosage form containing both agents. When administered as a combination, the therapeutic agents can be formulated as separate compositions that are given at the same time or different times, or the therapeutic agents can be given as a single composition.

It is to be understood that this invention is directed to compositions and combined therapies as described herein, for any disease, disorder or condition, as appropriate, as will be appreciated by one skilled in the art. Certain applications of such compositions and combined therapies have been described hereinabove, for specific diseases, disorders and conditions, representing embodiments of this invention, and methods of treating such diseases, disorders and conditions in a subject by administering a compound as herein described, alone or as part of the combined therapy or using the compositions of this invention represent additional embodiments of this invention.

In another embodiment, acute or chronic skin conditions treated via the methods and uses of this invention may comprise lesions suffered in trauma, burns, abrasions, surgical incisions, donor graft sites, and/or lesions caused by infectious agents.

In another embodiment, the acute or chronic conditions of the skin may comprise chronic venous ulcer, diabetic ulcer, compression ulcer, pressure sores, and ulcers or sores of a mucosal surface.

In another embodiment, the acute or chronic condition of the skin may comprise surface lesions caused by a persistent inflammatory condition or infection, or by a genetic defect (such as Haloid formation and coagulation abnormalities).

In one embodiment, the methods of healing of wounds, burns, abrasions or other acute or chronic conditions of the skin comprises administering a composition comprising the fruit and vegetable product as herein described to stimulate or enhance exfoliation of damaged skin cells, cell proliferation or migration at the treatment site, increase in density of epithelial cells at the site as a result of the applied therapy and thereby closure of a wound if present, or restoration of normal physiological function.

In one embodiment, this invention contemplates manipulation of the skin and repair of any imperfection of the skin surface for other purposes, such as cosmetic enhancement.

In another embodiment, compounds and compositions as herein described may be utilized for protecting skin from UV radiation, or palliative treatment of damage thereby. In some embodiments, the compositions are beneficial as a radiation therapy or as a sunscreen.

In another embodiment, the methods and compositions of the invention can be used in treating hair conditions, in preserving hair color, hair shine or quality. In some embodiments, methods and compositions of the invention can be used in treating hair loss, or as adjunctive therapy with hair replacement and hair loss treatment protocols.

In some embodiments, the compositions of this invention provide the beneficial effects described herein as a consequence of their inclusion of whole fruits and vegetables. In some embodiments, the mechanism whereby the compositions of this invention exert their effect is via promoting skin peeling or exfoliation to remove damaged or injured skin, and providing an environment during a skin healing process which is beneficial or promotes skin healing.

EXAMPLES

Example 1

Preparation of Embodiments of Compositions of this Invention

Fruit and vegetables are weighed, cut and boiling water is added to the cut fruits and vegetables. The resulting mixture is filtered through a metal sieve, cooled to a temperature of a range between about 45-55° C., and combined with other components of the composition, such as, for example, preservatives, fragrance, etc. Moisturizers and emollients may be added, as well. In some instances, a raw concentrated product is prepared, which is then incorporated within available cosmetic or topical formulations.

Compositions comprise a derivative of at least one *Beta* species, present at a concentration of 0.1-5% w/w, at least one *Capsicum* species, present at a concentration of 0.1-5% w/w and at least one *Malus* species present at a concentration of 1.5-10% w/w in said composition.

Compositions comprise a derivative of at least one *Beta* species, present at a concentration of 0.2-1% w/w, at least one *Capsicum* species, present at a concentration of 0.2-1% w/w and at least one *Malus* species present at a concentration of 2.7-3.3% w/w in said composition.

The composition may further comprise at least one *Citrus paradisi* present at a concentration of 4.0-6% w/w, *Citrus limon* present at a concentration of 4.0-6% w/w, a Diospyros species present at a concentration of 3.5-6% w/w, a *Carica papaya* species present at a concentration of 2.5% w/w, a Solanum species present at a concentration of 2.3-2.8% w/w, at least one Cucumis species is present at a concentration of 1.2-1.5% w/w.

Example 2

Preparation of Composition 1 Useful in the Treatment of Eczema and Diabetic Lesions A basic fruit and vegetable composition was prepared as described in Example 1. The composition contained (expressed as percent w/w in the total composition):
Grapefruit: 4.9
Lemon: 4.9
Persimmon: 4.2
Apple: 3.3
Tomato: 2.8
Cucumber: 1.5
Hot Pepper: 0.2
Red Beet: 0.2

Example 3

Preparation of Composition 1 Useful in the Treatment of Psoriasis

A basic fruit and vegetable composition was prepared as described in Example 1. The composition contained (expressed as percent w/w in the total composition):
Grapefruit: 4.8
Lemon: 4.8
Apple: 3.2
Tomato: 2.7
Cucumber: 1.4
Hot Pepper: 1.0
Red Beet: 1.0

Example 4

Treatment of Psoriasis

A composition was prepared as described in Example 3 and was applied daily to the arms and legs of a subject suffering from psoriasis. Patients with Psoriasis Guttate, Pustalar and nose with scalp psoriasis were included. Untreated skin is heavy with scale, and potentially severe bleeding from cracks on the skin. The same subject was treated on some lesions with the compositions of this invention and some lesions were left untreated. 16 subjects were treated with the composition. More than 83% of the treated subjects showed marked improvement in response to treatment following one month of treatment, with only minor side effects reported.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. A topical fruit and vegetable extract composition for treating a skin disease comprising therapeutically effective amounts of a *beta* extract, a *Capsicum* extract, a *Malus* extract, a Solanum extract, a Cucumis extract, a *Citrus paradise* extract, and a *Citrus limon* extract, wherein the *beta* extract is an extract of a beta selected from the group consisting of *Beta vulgaris*, chard, spinach beet, sugar beet, and mangel-wurzel, wherein the *Capsicum* extract is an extract of a *Capsicum* selected from the group consisting of *Capsicum annuum, Capsicum frutescens, Capsicum chinense, Capsicum pubescens, Capsicum baccatum*, and cultivars thereof, wherein the *Malus* extract is an extract of a *Malus* selected from the group consisting of *Malus demestica, Malus sieversii, Malus baccata, Malus sylvestris*, and cultivars thereof, wherein the Solanum extract is an extract of *Solanum lycopersicum* or a cultivar thereof, wherein a Cucumis extract is an extract of *Cucumis sativus* or a cultivar thereof, and wherein said extracts are from a plant part selected from the group consisting of pulp, seeds, zest, and peel, and combinations thereof, wherein said composition has a pH in the range of about 4.2 to about 5.5.

2. The topical fruit and vegetable extract composition of claim 1, further comprising an extract of *Prunus persica* or a cultivar thereof.

3. The topical fruit and vegetable extract composition of claim 1, further comprising an extract of *Diospyros kaki, Diospyros lotus*, or a cultivar thereof.

4. The topical fruit and vegetable extract composition of claim 1, further comprising a *Citrus maxima* extract.

5. The topical fruit and vegetable extract composition of claim 1, further comprising a *Carica papaya* extract.

6. The topical fruit and vegetable extract composition of claim 1, wherein the *Beta* extract is present at a concentration of 0.1-5% w/w, the *Capsicum* extract is present at a concentration of 0.1-5% w/w, the *Malus* extract is present at a concentration of 1.5-10% w/w, the Solanum extract is present at a concentration of 1.0-10% w/w, the Cucumis extract is present at a concentration of 0.1-10% w/w, the *Citrus paradisi* extract is present at a concentration of 2.0-10% w/w, and the *Citrus limon* extract is present at a concentration of 2.0-10% w/w in said composition.

7. The topical fruit and vegetable extract composition of claim 6, further comprising an extract of *Diospyros kaki, Diospyros lotus*, or a cultivar thereof at a concentration of 1.0-10% w/w in said composition.

8. The topical fruit and vegetable extract composition of claim 6, further comprising a *Carica papaya* extract at a concentration of 0.1-5% w/w in said composition.

9. A method for treating a skin disease in a mammal, comprising topically applying to the mammal a therapeutically effective amount of the topical fruit and vegetable extract composition of claim 1.

10. The method of claim 9, wherein the topical fruit and vegetable extract further comprises an extract of *Prunus persica* or a cultivar thereof.

11. The method of claim 9, wherein the topical fruit and vegetable extract further comprises an extract of *Diospyros kaki, Diospyros lotus*, or a cultivar thereof.

12. The method of claim 9, wherein the topical fruit and vegetable extract further comprises a *Citrus maxima* extract.

13. The method of claim 9, wherein the topical fruit and vegetable extract further comprises a *Carica papaya* extract.

14. The method of claim 9, wherein the *Beta* extract is present at a concentration of 0.1-5% w/w, the *Capsicum* extract is present at a concentration of 0.1-5% w/w, the *Malus* extract is present at a concentration of 1.5-10% w/w, the Solanum extract is present at a concentration of 1.0-10% w/w, the Cucumis extract is present at a concentration of 0.1-10% w/w, the *Citrus paradisi* extract is present at a concentration of 2.0-10% w/w, and the *Citrus limon* extract is present at a concentration of 2.0-10% w/w in said composition.

15. The method of claim 14, wherein the topical fruit and vegetable extract further comprises an extract of *Diospyros kaki, Diospyros lotus*, or a cultivar thereof at a concentration of 1.0-10% w/w in said composition.

16. The method of claim 9, wherein the topical fruit and vegetable extract further comprises a *Carica papaya* extract at a concentration of 0.1-5% w/w in said composition.

17. The method of claim 9, wherein the skin disease is psoriasis.

18. The method of claim 9, wherein the skin disease is acne, seborrhea, eczema, diabetic ulcers or lesions, wrinkles or skin fissures.

* * * * *